United States Patent [19]

Vézina et al.

[11] Patent Number: 5,990,385
[45] Date of Patent: Nov. 23, 1999

[54] PROTEIN PRODUCTION IN TRANSGENIC ALFALFA PLANTS

[75] Inventors: Louis-P. Vézina; Serge Laberge; Renée Bazin; Habib Khoudi; Réal Lemieux; Guy Allard, all of Sainte-Foy, Canada

[73] Assignees: Her Majesty the Queen in right of Canada, as represented by the Minister of Agriculture and Agri-Food, Ottawa; Canadian Red Cross Society; Universite Laval, both of Sainte-Foy, all of Canada

[21] Appl. No.: 08/968,688

[22] Filed: Nov. 12, 1997

[51] Int. Cl.$^6$ .............................. A01H 1/02; C07K 1/14; C07K 1/22; C12N 15/13; C12N 15/82

[52] U.S. Cl. .................... 800/278; 435/69.1; 435/69.6; 530/412; 530/413; 800/260; 800/288

[58] Field of Search .............................. 435/172.3, 430.1, 435/419, 69.1, 69.6, 468; 800/205, 250, 69.1, 69.6, 260, 278, 288, 298; 530/412, 417, 413; 536/23.53

[56] References Cited

U.S. PATENT DOCUMENTS 5,639,947   6/1997   Hiatt et al. ............................... 800/205

FOREIGN PATENT DOCUMENTS

| 0 657 538 A2 | 6/1995 | European Pat. Off. . |
| WO 96/21012 | 7/1996 | WIPO . |
| WO 96/22372 | 7/1996 | WIPO . |

OTHER PUBLICATIONS

Hiatt A, et al. "Plantibodies: Expression of monoclonal antibodies in plants."Antibody Expression and Engineering: A Practical Guide, 1992.

Darnell J, et al. Molecular Cell Biology, pp. 78–80, 1986.

An, G., et al., 1988. *Plant Mol. Biol. Manual*, Gevin, S.B., and Shilperoot, R.A. (eds) Kluwer Academic Publisher, Dordecht, pp. A3/1–19.

Austin S., et al., 1997. "The Potential use of transgenic Alfalfa as a Bioreator for the Production of Enzymes" *Biotechnology and the Improvement of Forage Legumes*. McKersie B.D. And Brown D.C.W. (eds) CAB International, pp. 409–418.

Bradford, M.M. 1976. "A Rapid and Sensitive Method for the Quantitation of Microgram Quantities of Protein Utilizing the Principle of Protein Dye Binding" *Anal Biochem* 72: 248–254.

De Wilde, C., et al., 1996. "Interact antigen–binding MAK33 antibody and Fab fragment accumulate in intracellular spaces of *Arabidopsis thaliana*". *Plant Science*, 114:233–241.

de Vries, S., et al., 1988. "Isolation of total and polysomal RNA from plant tissues," *Plant Mol. Biol. Manual*, Gevin, S.B., and Shilperoot, R.A. (eds) Kluwer Academic Publisher, Dordrecht, PMAN–B6/1–13.

Desgagnes, R., et al.,. 1995 "Genetic transformation of commercial breeding lines of alfalfa (Medicago sativa)", *Plant Cell Tissue Organ Culture*. 42:129–140.

During, K., et al., 1990. "Synthesis and self–assembly of a functional monoclonal antibody in transgenic *Nicotiana tabacum*", *Plant Mol. Biol.* 15:281–293.

Grierson, D. and Covey, S. (1988), *Plant Molecular Biology, 2d Ed.*

Hiatt, A., Cafferky, R., and Bowdish, K. 1989. "Production of antibodies in transgenic plants", *Nature* 342:76–78.

Hiatt, A. 1990. "Antibodies produced in plants", *Nature* 344:469–470.

Hiatt, A., and Pinney, R., 1992. pp. 159–176 "Expression of Monoclonal Antibodies in Plants," *Antibody expression and engineering: A practical guide*. Borrebaeck, C.A.K. (ed) Frreman W.H. and company, New York.

Issit, P.D. 1985. *Applied Blood Group Serology: Third Edition*. Montgomery Scientific Publication, Miami.

Jones, B.A. et al. 1995. "Characterization of proteolysis in alfalfa and red clover," *Crop Sc.* 35:537–541.

(List continued on next page.)

*Primary Examiner*—Lynette Smith
*Assistant Examiner*—Amy J. Nelson
*Attorney, Agent, or Firm*—Oliff & Berridge, PLC

[57] ABSTRACT

This invention is directed to characterizing a host system suitable for the production of functional transgenic proteins, such as anti-human IgG, for use in applications requiring Government regulatory approval. It is well known that regulatory agencies required stable, consistent master cell banks and master cell lines for the production of transgenic proteins in order to ensure sufficient material for appropriate characterization, clinical trials, and potential sales. Current plant production systems require the establishment of seed banks for this purpose. However, there are many draw backs related to such a system for the production of a continuous reliable transgenic protein source. An aspect of this invention is directed to characterizing a plant production system suitable for transgenic proteins that meet the stringent regulatory requirements. Another aspect of this invention exemplifies the production and characterization of an anti-human IgG for use as a blood grouping reagents, through the expression of corresponding genes in transgenic alfalfa plants. The cDNAs of the heavy and light chains of a human IgG-specific IgG2a(kappa) murine mAb (C5-1) were transferred into alfalfa through Agrobacterium infection. Transgenic plants expressing the light- and heavy-chain encoding mRNAs were obtained and plants from the F1 progeny (obtained by sexual crossing) were found to express fully assembled C5-1. Furthermore, the transgenic protein was stable in vivo, as well as during extraction and purification procedures. Purification yielded a unique H2L2 form with a reactivity indistinguishable from hybridoma-derived C5-1 in standardized serological tests. Results indicate that plant-derived transgenic proteins, such as mAbs can be used as diagnostic reagents as effectively as hybridoma-derived mAbs, and demonstrates the usefulness of the transformed alfalfa system to produce large amounts of proteins, including multimeric proteins such as mAbs.

10 Claims, 8 Drawing Sheets

OTHER PUBLICATIONS

Ma, J.K.–C., et al., 1994. "Assembly of monoclonal antibodies with IgG1 and IgA heavy chain domains in transgenic tobacco plants," *Eur. J. Immunol.* 24:131–138.

McKersie, B.D., and Bowley, S.R. 1993. "Synthetic Seeds of Alfalfa," pp. 231–255 Redenbaugh (ed) CRC Press.

Miele, L. 1997. "Plants as bioreactors for biopharmaceuticals: regulatory considerations," *TIBTECH* 15: 45–50.

Morris, P., and Robbins, M.P. 1997. "Manipulating and Condensed Tannins in Forage Legumes," *Biotechnology and the Improvement of Forage Legumes.* McKersie, B.D. and Brown D.C.W. (eds) CAB International, pp. 147–173.

Papadopoulos, Y.A., McKersie, B.D., 1983. "A comparison of protein degradation during wilting and ensiling of 6 forage species," *Can. J. Plt. Sc.* 63: 903–912.

St. Laurent, M., et al., 1993. "Functional Cooperation Among Human IgG–specific Murine Monoclonal Antibodies for the Detection of Weak Blood Group Antibodies in Routine Agglutination Tests," *Vox Sang.* 64: 99–105.

Wang, H.Y., and Imanaka, T. 1995. "Antibody expression and engineering", American chemical Society, Washington, D.C.

Rogers, Stephen G. et al., (1988) "Gene Transfer in Plants: Production of Transformed Plants Using Ti Plasmid Vectors," *Methods for Plant Molecular Biology*, Academy Press, New York VIII, pp. 421–463.

Whitelam, G.C., and Cockburn, W. 1996. "Antibody expression in transgenic plants," *Trends in Plant Science.* 8: 268–272.

Wongsamuth, R. and Doran, P., "Production of Monoclonal Antibodies by Tobacco Hairy Roots," *Biotechnology and Bioengineering.* 54, 1997, 401–415.

Wright, A., Shin, S–U and Morrison, S.L. 1992. "Genetically engineered antibodies: progress and prospects," *Critical Review in Immunology* 12: 125–168.

Firek, Simon et al., "Secretion of a Functional Single–Chain Fv Protein in Transgenic Tobacco Plants and Cell Suspension Cultures", *Plant Molecular Biology* 23: 861–870, 1993, pp. 861–870.

Hiatt, Andrew et al., "Monoclonal Antibody Engineering in Plants", FEBS Letters, vol. 307, No. 1, 1992, pp. 71–75.

Ma, Julian K.C., et al., "Generation and Assembly of Secretory Antibodies in Plants", *Science*, vol. 268, May 5, 1995.

"Abstracts $4^{th}$ International Congress of Plant Molecular Biology", The International Society for Plant Molecular Biology, Amsterdam, Jun. 19–24, 1994.

Michaud, Réal et al., "Report of the Thirty–Fourth North American Alfalfa Improvement Conference", University of Guelph, Guelph Ontario, Ul. 10–14, 1994.

Ma, K–C. J., "Antibody Expression in Plants", 1995 American Chemical Society.

Ma, K–C. J., "Immunotherapeutic Potential of Antibodies Produced in Plants", TIBTECH, vol. 13, Dec. 1995, pp. 522–527.

Vézina, Louis–P., "Call for Abstracts", 1997 Congress on In Vitro Biology, Washington, D.C., Jun. 14–18, 1997.

A  B

PROTEIN PRODUCTION IN TRANSGENIC ALFALFA PLANTS

The present invention relates to the production of transgenic proteins in alfalfa plants. More specifically this invention relates to the production of multimeric proteins within transgenic alfalfa plants for use in a range of applications such as diagnostic assays.

BACKGROUND OF THE INVENTION

Full citations for references appear at the end of the examples section.

The use of proteins for use in a range of pharmaceutically related applications is subject to stringent regulatory requirements established by the Government. For example, in the U.S, the Center for Biologics Evaluation and Research (CBER) publishes a set of documents outlining the requirements regarding the production and monitoring of proteins produced transgenically (see fttp://www.fdagov/cber/cberftp/html), a similar set of regulations are related to the production and use of biologics in Canada. The CBER documents indicate that a biologic be produced from a reliable and continuous source, in order to ensure that a consistent product is obtained (ftp://ftp.fda.gov/cber/ptc/ptc_mab.txt). This is because the product must be extensively tested and verified prior to its approval for use, and be available in the same form for future sales. There are several well established expression systems for the production of a biologic including master cell banks for cell culture, seed banks for transgenic plants, virus seed stocks for transgenic expression systems, and founder strains for transgenic animals. Master vector seed stocks must be generated for the use of transient expression systems, with the stability of the expression constructs routinely tested. If a protein such as a monoclonal antibody is to be produced from a cell line, documentation regarding the characterization of the parent cell line, cell production protocols, purification and quality control are required both of the master cell bank and working cell bank. Any changes to the manufacturing or formulation, especially if clinical trials are initiated require extensive re-characterization of the master and working cell banks and product, since these changes may result in significant changes of biological activity. It is stated within the CBER document "Points to Consider in the Manufacture and Testing of Monoclonal Antibody Products for Human Use" (Feb. 28, 1997), that "[i]t is recommended that the material used in the preclinical studies be manufactured using the same procedures as used or intended for use in manufacturing material for clinical trials". Furthermore, if any scale up is to take place, for example for Phase 2 studies, "that product comparability may have to be demonstrated . . . [which] may or may not require additional clinical studies" (ftp://ftp.fda.gov/cber/ptc/ptc_mab.txt).

Plants have been used for the production of transgenic proteins, however, the same considerations that apply to the maintenance of master cell lines as discussed above, apply to the plant equivalent (see Miele, 1997). Seed banks for transgenic plants require periodic amplification since seeds can not be stored indefinitely. The storage of seed stocks must reduce potential genetic damage of the transgene of interest. Any other factors that may affect the seed bank must also be controlled including contamination of the seed by insects, fungi or bacteria. Furthermore, the stability of the transgene must be determined, as well as the levels of product expression in representative plants of a given seed lot, or between seed lots following reamplification of the seed bank. Additional data may also be required that compares the product prepared from different seed banks. This latter characterization also applies to year to year variations in harvested seed stocks. In general product development requires the constant monitoring of the biochemical and biological properties of the transgenic product (Miele, 1997). When these criteria are coupled to plant systems for the production of multimeric proteins the problem is compounded, since, in order to produce hybrid seeds capable of producing multimeric proteins, transgenic plants obtained from homologous seed lots, which require re-amplification and maintenance as outlined above, need to be crossed in order to produce the final hybrid seed, which again must be maintained as defined above. Clearly an alternate source of transgenic protein that is stable, and results in a continuous supply of protein without necessitating the extensive maintenance of multiples of seed banks is required.

The preparation of transgenic proteins with plants is well established within the literature and several successful transformation systems have been established. For example, multimeric proteins have been prepared via sexually crossing progeny of tobacco plants (Hiatt 1990, Hiatt and Pinney, 1992; Ma et al 1995), however, all plant sources to date that have been used for transgenic protein production for pharmaceutical applications have utilized annual plants. This necessitates the constant reamplification and reverification of seed bank stocks as described above. Clearly if an perennial plant species is utilized for the generation of transgenic proteins, the overall maintenance costs, and lot-to-lot variability would be greatly reduced. Furthermore, if vegetative structures of the perennial plant are harvested as a source of the transgenic protein, the regulatory requirements are reduced even more. In order to ensure the production of a perennial source of transgenic protein many factors must be taken into account that relate to the above requirements regarding reliability consistency of the product derived from a stable, continuous source.

One of the most important blood grouping reagents is the anti-human IgG reagent used for the detection of non-agglutinating antibodies. Mouse mAbs with suitable anti-human IgG specificity have been obtained and are gradually replacing the rabbit polyclonal anti-human IgG traditionally used in the Coombs' reagent (St Laurent et al 1993). These mAbs are produced by large-scale culture of B cell hybridomas. While reliable, this process is costly due to the need for sophisticated equipment, expensive culture media and trained personnel. In comparison with other diagnostic applications of mAbs, the market for proteins used in blood bank testing is highly competitive; consequently, prices for proteins are relatively low and the cost-efficiency of mAb production has become a critical issue.

The isolation of cDNA clones encoding the light and heavy chains of mAbs has allowed the expression of antibody genes in various heterologous systems including bacteria, fungi, insect cells, plants and non-lymphoid mammalian cells (Wang et al 1995; Wright et al 1992.). Amongst these systems, plants appear to be one of the most promising for cost-efficiency. However, following the initial demonstration in tobacco, it became important to find crop plants in which this technology could be brought to face modern demands for marketability. Hiatt et al (WO 96/21012, published Jul. 11, 1996) disclose methods for, and the preparation of therapeutic immunoglobulins ("protection proteins"), for use against mucosal pathogens, in plants. In EP 0 657 538, Galeffi and Natali disclose the production of antibodies for therapeutic or diagnostic use that recognize HER-2 oncogene present in mammary and ovary tumours. It is important to find crop plants in which recombinant proteins can be produced and that can face modem demands for marketability. These demands not only include competitivity of production costs, but also reliability, which implies that unless long-term stable supplies of the purified recombinant molecule can be established, means of insuring the perenniality of the homologated source material from which clonal populations can be derived must be developed. For B cell hybridomas, perenniality is insured by the establishment of a master cell bank, which consists of aliquots of cells taken from homogeneous pool and cryopreserved in liquid nitrogen. Hiatt (1990) suggests that alfalfa, soybean, tomato and potato may be useful alternatives as hosts for the propagation of antibodies. Alfalfa is one of the cheapest plant biomass to produce in current agro-ecosystems, and its perenniality in most climatic conditions makes it an attractive crop for sustainable agriculture. Furthermore, alfalfa (*Medicago sativa* L.) does not require annual tilling and planting, and the use of residual plant tissue for animal feed is well established (Austin and Bingham, 1997). However, several studies have examined the degree of proteolysis in ensiled forage species, and it known that proteolysis is more extensive in legume forages species than in grass species, with alfalfa exhibiting the highest rate and extent of proteolysis (Jones et al, 1995; Papadopoulos and McKersie, 1983). Furthermore, it is well known within the art that not all alfalfa plants are perennial, and of the perennial alfalfa plants not all are amenable to transformation protocols (Desgagnés, 1995).

The stability of transgenic proteins within plant tissues, and upon its extraction has been of concern in the literature. However, little is known about antibody stability in plant cell systems (Wongsamuth and Doran, 1997). Several workers (Hiatt et al (1989), During et al (1990), Ma et al (1995), Ma and Hein (1995), Schouten (1996)) have observed that chimeric constructs containing signal sequences for directing co-translational insertion of the constructs within the endoplasmic reticulum increase the stability of constructs within transgenic plants. In the absence of leader sequences, transgenic protein recovery is very low (Hiatt et al, 1989). It is a general practice to include protease inhibitors within the extraction cocktails in order to maximize protein recovery from transgenic plant tissues. However, marketable production of transgenic proteins from plants requires simplicity. For example, Austin and Bingham (1997) review large scale maceration and juice extraction protocols at the field site with final processing taking place at a processing plant several hours later. Such protocols employ the use of water and mechanical maceration and would be impractical if proteolysis within the extract was of concern, or if protease inhibitors were required during extraction. This is especially true for the application of alfalfa species known to exhibit high rates of proteolysis, especially after harvest (Jones et al 1995; Papadopoulos and McKersie 1983).

One kg of mAb has a present market value of $1,000,000 to $10,000,000. When production costs are estimated per gm of C5-1 produced under greenhouse conditions, including heating, manpower and consumables for extraction and purification, in a 250 $m^2$ with an expected yield of 100 g per year, the cost per g of C5-1 would be between $500–$600, yet yield a market value of $400,000. Such estimates demonstrate that recombinant proteins could be produced cost-effectively in plants, however, a suitable plant system needs to be established. An aspect of an embodiment of this invention is directed to determining the characteristics required for a suitable transgenic plant line that can be used to produce a transgenic protein of interest that meets many of the criteria established within the CBER recommendations for a biologic compound.

SUMMARY OF THE INVENTION

This invention is directed to the production of transgenic proteins in alfalfa plants.

This invention is also directed to a method for the production of protein for use in serological assays comprising transforming an alfalfa plant with a gene of interest that encodes the protein, and selecting transformed alfalfa plants that express the protein, or progeny of selected alfalfa plants, and extracting the protein from the transformed plant. An aspect of an embodiment of this invention relates to the purification of the protein using affinity chromatography.

This invention also relates to a method for the production of a monoclonal antibody to be used in red cell serology, comprising:

a) transforming alfalfa with a vector, comprising a gene encoding a monoclonal antibody to produce a transformant, b) screening the transformant for the presence of the transgenic gene, c) growing the transformant so as to produce the monoclonal antibody encoded by the transgenic gene, d) harvesting aerial portions of said transgenic alfalfa plant, e) extracting said monoclonal antibody from desired tissues of the transgenic alfalfa, f) allowing the transgenic alfalfa plant to re-grow, and g) repeating steps c) to f), and optionally propagating the transgenic plant. This invention is also directed to this method wherein the step of optionally propagating the transgenic plant includes any clonal propagation method including stem or embryogenic propagation. A further aspect of an embodiment of this invention relates to purifying the monoclonal antibody using affinity chromatography.

This invention also includes a monoclonal antibody produced by this method.

This invention is also directed to a method of producing a protein of interest within transformed alfalfa, comprising;

a) transforming a suitable alfalfa genotype with a vector containing a gene encoding the protein of interest to produce a transformant, b) screening the transformed suitable alfalfa genotype for the presence of the transgenic gene, c) growing the transformed suitable alfalfa genotype so as to produce the protein of interest, d) harvesting aerial portions of the transgenic suitable alfalfa genotype, e) extracting the protein of interest from desired tissues of the transgenic suitable alfalfa genotype, f) allowing the transgenic suitable alfalfa genotype to re-grow, and g) repeating steps c) to f).

This invention is also directed to transgenic alfalfa plants capable of expressing multimeric, biologically active proteins.

Although the present invention is exemplified by the preparation of a monoclonal antibody C5-1, in practice any product of interest can be prepared within transformed alfalfa following the protocols of this invention. Advantages to using a suitable alfalfa genotype for the expression of transgenic proteins which have not been disclosed within the prior art include the stability of proteins within:

1) harvested tissues obtained from the plant and left to air dry and stored prior to extraction;
2) extracts harvested in water at room temperature and in the absence of stabilizers, protease inhibitors, buffers, salts, antioxidants, reducing agents, stabilizers or other additives typically added to extract cocktails to ensure protein stability and activity;
3) the same plant over repeated harvests within a growing season, and between growing seasons; and within
4) clonal propagules.

Furthermore, as alfalfa is a perennial plant, capable of vegetative propagation, clonal material may be obtained and harvested over substantial lengths of time spanning many growing seasons. This ensures a stable source of proteins of interest within transgenic alfalfa. Such features are not found within other typically used plants for transgenic protein production which tend to be annuals including tobacco, Arabidopsis, soybean and maize. However, not all alfalfa varieties are perennial, and many of the varieties that are both perennial and high yielding (agronomically speaking) are known to be recalcitrant to transformation protocols. Therefore, this invention is also directed to a method for the selection of suitable alfalfa lines or genotypes for use in producing transgenic proteins comprising:

(a) screening a library of alfalfa genotypes or lines to determine genotypes or lines that are perennial;
(b) screening the selected lines or genotypes identified in (a) for embryogenic potential;
(c) screening the selected lines or genotypes identified in (b) for transformability;
(d) screening the selected lines or genotypes identified in (c) for stability of the transgenic protein.

This invention is also directed to suitable alfalfa genotypes, or propagules derived from the suitable alfalfa genotype, for producing transgenic proteins that are useful in meeting regulatory approval requirements for Biologics. The suitable alfalfa genotype is characterized as being perennial, exhibiting embryogenic potential, is transformable, and does not degrade the transgenic protein so that the protein is stable in vivo, in dried areal tissues, as well as during extraction procedures. Furthermore, this invention encompasses propagules of the suitable alfalfa genotype including clonally-derived propagules such as stem, or embryo-derived propagules.

BRIEF DESCRIPTION OF THE DRAWINGS

These and other features of the invention will become more apparent from the following description in which reference is made to the appended drawings wherein:

FIG. 1A, Extracts from plants transformed with pGA643-kappa were hybridized with a radiolabeled probe (600 bp) derived from the kappa cDNA. Lanes 1,2 and 4 to 9 contain RNA extracts from transgenics; lane 3 contains RNA from untransformed genotype 11.9. FIG. 1B, Extracts from plants transformed with pGA643-gamma were hybridized with the entire radiolabeled gamma cDNA. Lanes 1–5 contain RNA extracts from transgenics; lane 6 contains RNA from untransformed 11.9. FIG. 1C Extracts from plants of the F1 progeny were hybridized with a mixture of both the kappa and gamma probes. Lanes 1–5 and 7 contain RNA extracts from transgenics; lane 6 contains RNA from untransformed 11.9.

DESCRIPTION OF PREFERRED EMBODIMENT

Figure 1A:
FIGS. 1A–1C show the expression of C5-1 mAb cDNAs in transgenic alfalfa plants. Total RNA (15 µg/per lane) isolated from transgenic and control plants was separated on 1% agarose formaldehyde gels and transferred onto Hybond-N nylon membranes. The size of the transcripts are shown in kilobases. Autoradiograms were produced by exposure at −70° C. for 24 h.

The present invention is directed to the production of proteins within transgenic alfalfa plants.

According to the present invention, by "gene of interest" it is meant a gene that is capable of encoding a protein. However, this definition also applies to genes of interest for which the combined transcriptional and translated products lead to the production of a multimeric protein(s), for use as a Biologic, such as within serological assays. A gene of interest can be used to transform alfalfa using established protocols (e.g. Desgagnés et al, 1995). Despite the complexity of the alfalfa genome, traits acquired through Agrobacterium-mediated gene transfer are stable and transmitted sexually following a simple Mendelian pattern (Desgagnes et al, 1995). This characteristic is essential for the production of proteins including multimeric proteins. Without wishing to limit the types of proteins that may be produced using the present invention in any manner, an example of a multimeric protein may be a mAb such as C5-1. The production and properties of this protein are exemplified below.

By "a promoter" it is meant the region of a DNA sequence active in the initiation and regulation of the expression of a gene under the control of the promoter region, as it is typically understood by one of skill in the art. This sequence of DNA, usually upstream (5U) to the coding sequence of a structural gene, controls the expression of the coding region by providing the recognition for RNA polymerase and/or other factors required for transcription to start at the correct site.

There are generally two types of promoters, inducible and constitutive. An "inducible promoter" is a promoter that is capable of directly or indirectly activating transcription of one or more DNA sequences or genes in response to an inducer. In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible promoter may be exposed to an inducer by externally applying the inducer to the cell or plant such as by spraying, watering, heating or similar methods. In addition, inducible promoters include tissue specific promoters that function in a tissue specific manner to regulate the gene of interest within selected tissues of the plant. Examples of such tissue specific promoters include seed, flower or root specific promoters as are well known in the field.

By "constitutive promoter" it is meant a promoter that directs the expression of a gene throughout the various parts of a plant and continuously throughout plant development. Examples of known constitutive promoters include those associated with the CaMV 35S transcript and Agrobacterium Ti plasmid nopaline synthase gene.

Gene constructs of the present invention comprise a 3U untranslated region. A 3U untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3U end of the mRNA precursor. Polyadenylation signals are commonly recognized by the presence of homology to the canonical form 5U AATAAA-3U although variations are not uncommon. Non-limiting examples of suitable 3U regions are the 3U transcribed non-translated regions containing a polyadenylation signal of Agrobacterium tumour inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene.

The gene constructs of the present invention can also include other optional regulatory motifs such as enhancers, either translation or transcription enhancers, as may be required. These enhancer regions are well known to persons skilled in the art, and can include, for example, the enhancer region of the 35S regulatory region, as well as other enhancers obtained from other regulatory regions, and/or the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the constructs of this invention may be further manipulated to include plant selectable markers. Useful selectable markers include, but are not limited to, enzymes which provide for resistance to an antibiotic such as gentamycin, hygromycin, kanamycin, and the like. Similarly, enzymes providing for production of a compound identifiable by colour change such as GUS ($-glucuronidase), or luminescence, such as luciferase are useful.

Also considered part of this invention are transgenic plants containing the chimeric gene construct of the present invention. This invention is also directed to parts obtained from transgenic plants that express the gene of interest, for example leaf, stem, seed, flower or root. These selected parts of plants may be obtained from plants transformed with vector comprising either constitutive or inducible promoters. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, embryo or shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach (1988) and Geierson and Corey (1988). The present invention further includes a suitable vector comprising the chimeric gene construct, and related 5' and 3' regulatory regions involved in the expression of said gene construct.

By "suitable alfalfa line" or "suitable alfalfa genotype" it is meant a genotype or line of alfalfa that is perennial, exhibits embryogenic potential (for example at least 1 embryogenic calluses per 20 leaf discs or other explant tissue), is transformable, and in which transgenic proteins are stable following the criteria of stability as discussed throughout this document (also see Example 3). Not all alfalfa genotype or lines are perennial, and it is well known that many perennial genotype or lines of alfalfa are non-embryogenic and non-transformable, or that these properties may change upon transformation (Desgagnes, 1995). Even though alfalfa plants appear desirable as a host plant due to the advantages described earlier, alfalfa plants are known to exhibit high protease activity. In fact of the characterized forage species, legume forages exhibit a higher degree of proteolysis during ensiling than grass species, and alfalfa exhibits the highest extent and rate of proteolysis of the legume forages (Jones et al. 1995). Furthermore, it has been demonstrated that transgenic proteins in other plant species, such as tobacco are readily degraded by endogenous proteolytic activity (e.g. Hiatt et al, 1989). When one considers these two factors in combination, it is totally unexpected that suitable alfalfa genotypes could be isolated that exhibit the property of ensuring transgenic protein stability. Therefore, it is important to determine whether any proteolytic activity within a suitable alfalfa genotype is directed to a transgenic protein of interest that is produced within the plant. In order to ensure acceptable proteolytic activity, certain minimum standards should be obtained. These minimum standards will vary as required by the applications of the transgenic proteins of interest. For example, if large quantities of the transgenic protein are required, the protein should be stable in aqueous extracts, preferably in the absence of any added component such as protease inhibitors, or other reagents typically added to extraction solutions. It may also be required that the transgenic protein be stable in drying and dry harvested tissues, allowing for large scale harvesting of the plant.

Suitable alfalfa genotypes or lines are obtained by screening a library of alfalfa plants to determine those that are perennial, then screening these selected genotypes or lines for embryogenic potential, followed by screening the selected genotypes or line for transformability. These plants are then transformed using a protein of interest and the stability of the protein in crude extracts and within dried aerial tissues is determined. This is then, optionally, followed by the step of verifying the utility of the transgenic protein for use as a Biologic. For the purposes of exemplifying the present invention, a embryogenic alfalfa genotype, 11.9, was characterized, however other genotypes could also have been used. This genotype was established to be perennial, embryogenic, transformable, and as indicated below, exhibit negligible proteolytic activity against transgenic proteins. However, it is to be understood that this genotype is to be considered as an example of possible alfalfa genotypes or lines that could be selected using the above criteria and this genotype is not meant to be limiting with regards to the application of the screening method, or plants obtained as a result of this screening protocol.

In order to explore cost effective methods for the preparation of proteins of interest that can be used in reagents, the production of transgenic proteins within a suitable alfalfa genotype or line was considered. As the mAb C5-1 has proved useful in red cell serology, the heavy and light chains of C5-1 were cloned from a library of hybridoma cell cDNAs and placed under the control of the 35S promoter prior to transforming alfalfa plants (see Example 1). However, it is to be understood that this mAb, and the use of the 35S promoter are provided as an example of a chimeric gene construct and a protein that may be used and produced within a suitable alfalfa genotype or line, respectively, and this example is not intended to be limiting in any manner.

The expression of C5-1 within suitable transgenic alfalfa plants was determined via Northern (FIG. 1) and Western (FIG. 5) analysis which confirmed that the gene was being expressed in transgenic tissues. The transgenically expressed mAb was stable in aerial tissues that were dried at room temperature or under field conditions over a several day period as determined by Western blots of extracted tissues (Example 3, FIG. 5). This mAb was also stable when co-extracted in the presence of alfalfa leaves, while co-extraction of C5-1 with tobacco leaves was significantly low (Example 3, FIG. 4). Similar results were also observed when other antibodies were co-extracted with alfalfa and incubated over periods of time (see Example 3, Tables 1 and 2). Furthermore, plant derived C5-1 displayed the same stability as hybridoma-derived C5-1 when injected intravenously into mice (FIG. 6), indicating a similar degree of protection is obtained due to glycosylation with the plant-derived, as that for the hybridoma-derived protein. These properties are important if large scale production and harvesting of proteins of interest is to be considered using alfalfa, since such procedures typically expose harvested tissues to long periods of air drying and simple aqueous extraction protocols.

Vegetative structures of some varieties of alfalfa are known to exhibit low levels of tannins (Morris and Robbins 1997). Without wishing to be bound by theory, the enhanced stability of proteins within tissue extracts of these alfalfas may be a result of the reduced levels of phenolics and tannins. These properties have been found to limit the use of alfalfa as a forage crop and initiatives are underway to increase the level of phenolics within this plant in order to increase its efficacy as a feed (Morris and Robbins 1997), however, these properties may be beneficial for the purposes disclosed for this invention.

Purification of plant C5-1 using affinity chromatography of the crude clarified extract revealed upon staining with Coomassie blue, that the final preparation was free of contaminants (see Example 2). This is a significant improvement from the methodologies reported previously (e.g. During et al 1990). There was also no apparent loss of C5-1 during the purification process and thus the yield from in planta C5-1 to purified C5-1 was estimated to more than 70%.

The immunoreactivity of purified plant-derived C5-1 was similar to its counterpart from hybridoma cells when tested in ELISA and standardized hemagglutination assays. Although several assembly types exist in crude extracts, the disclosed purification procedure yields a H2L2 form which is indistinguishable in terms of reactivity responses in serological tests as hybridoma-derived C5-1. This indicates that plant C5-1 could be used as a diagnostic protein as efficiently as hybridoma-derived C5-1.

For licensing a mAb-based protein, regulatory agencies require that the live material used for mAb production must be stable, to insure that quality and yield of the biologically active molecule does not vary over time (www.fda.gov/cber/cberftp/html; Miele, 1997). The stability of C5-1 between plant propagules was examined by determining the concentration of C5-1 within regenerants obtained from two genotypes from F1 progeny and comparing these levels to that within the parent material (see Example 3). These results indicate that concentrations of C5-1 within plant tissues remains constant between propagules and that such transgenic alfalfa lines appear to be a stable source of C5-1 mAb. Genotypes with high embryogenic potential like 11.9 can be induced in vitro to produce clonal propagules at high rates. The propagules can be brought into dormancy, desiccated to 15–20% water content, coated with an artificial endosperm and stored at −80° C. (McKersie and Bowley, 1993). This clonal material can be kept for years without significant loss of germinating potential and thus constitutes a cell bank from which material identical to the initial live material can be retrieved to initiate a new production cycle. It is also contemplated that other sources of clonal propagules, as would be known to one of skill in the art, may be used for the continued propagation of a suitable alfalfa genotype. Other sources may include, but are not limited to, embryo, stem, or other vegetative structures capable of being propagated.

Furthermore, as alfalfa is a perennial plant and capable of vegetative propagation, clonal material may be obtained and harvested directly form the field over substantial lengths of time spanning many growing seasons. This means that one plant may be repeatedly harvested over a 10 year period or more. This regenerative capacity and renewable availability of the same stock material ensures a consistent source of proteins of interest within transgenic alfalfa. Such capabilities and features are not found within other plants typically employed for transgenic protein production such as tobacco, Arabidopsis, soybean, Maize, or many genotype or lines of alfalfa.

The large-scale production of C5-1 mAb in transgenic alfalfa as commercial application of plantibody strategy is very promising since it represents an economical option compared to many heterologous systems including other plants. Furthermore, the use of a suitable alfalfa genotype provides the ability to minimize costs for characterizing and maintaining cell bank populations as required for approval and clinical trials of Biologics. Also, the purification of C5-1 mAb from transgenic alfalfa is similar to its purification from hybridoma supernatant.

At field scale, mature alfalfa stands contain between $1-3\times 10^6$ individual plants per hectare; this establishes the estimated production cost of clonal propagules to ca $8,000. According to our estimate of the antibody content in propagated transgenic alfalfa (0.13–1.0% of total soluble proteins), the yield of one hectare per year will be 500–1000 g. Alfalfa is a perennial crop and the field performance for this plant can be maintained for 3–4 years. This would bring production costs of the raw material to $3,000 per kg of mAb in an open-field exploitation. The production costs of one kg of C5-1 mAb by conventional hybridoma cell culture (about 50 mg of C5-1 mAb/L) is estimated to approximately 2 million dollars. Even if the antibody yield of hybridoma cultures was increased by a factor of 2040, the reduced costs (about 750 000$/kg) would still be significantly higher than the plant-derived C5-1.

There are as yet no reports on large-scale purification of mAbs from transgenic plant. Previous reports on purification of plant-derived mAbs showed that purification to homogeneity required sophisticated manipulations prior, and after affinity chromatography (During et al 1990). Scaling-up of the purification process of this invention was facilitated by the use of expanded bed adsorption chromatography. This technology produced a purified peptide from a large volume of roughly clarified extracts within a reduced time frame, and thus seems to open new approaches to the reduction of purification costs from colloidal extracts.

Moreover, the Coombs reagent is prepared with the unpurified supernatant from hybridoma cell cultures and thus partially purified plant preparations could be suitable for this diagnostic if prolonged stability is observed at 4° C.

EXAMPLES

The following method was derived for selecting a suitable alfalfa genotype or line for use in producing a transgenic protein of interest. Different steps of this method are described in more detail in subsequent examples. This method involves:

(a) screening a library of alfalfa genotypes to determine genotypes or lines that are perennial;
(b) screening the selected genotypes or lines identified in (a) for embryogenic potential;
(c) screening the selected genotypes or lines identified in (b) for transformability;
(d) screening the selected genotypes or lines identified in (c) for stability of the transgenic protein.

Plant material

Based on the selection of a perennial alfalfa with embryogenic potential, and transformability we had previously identified the genotype 11.9 which was isolated from a commercial breeding line (Desganes et al, 1995). In order to further ensure suitability of a plant selected as a result of the above criteria, experiments were carried out using this genotype as a model system to exemplify the utility of the present invention. However, the use of this genotype is not to be considered limiting in any manner. The use of genotype 11.9 is for the purposes of exemplifying the selection protocol, and properties of a selected plant with desirable properties. It is to be understood that the above selection protocol may be used for the selection of other alfalfa genotype or lines.

Bacterial strains, binary vector

The *E. coli* strain DH5" was used for DNA cloning. Plant transformations were carried out using a disarmed octopine strain of *Agrobacterium tumefaciens* (LBA4404). The binary plant expression vector pGA643 was used for DNA transfer (An et al 1988).

Selection of C5-1 hybridoma cell lines

Hybridoma cell lines were prepared by fusion of SP2/0 mouse myeloma cells with spleen cells of Balb/c mice hyper immunized with human IgG. The C5-1 hybridoma cell line was screened on the basis of reactivity of supernatant against weakly sensitized red blood cells as described previously (St Laurent, et al. 1993).

cDNAs isolation, sub-cloning and DNA constructs

The cDNAs of the heavy (H) and light (L) chains were cloned from a library of hybridoma cell cDNAs. After adding suitable restriction sites the fill-length cDNAs, including the 5' untranslated leader sequences were both sub-cloned into pGA643 under the transcriptional control of the 35S promoter to produce pGA643-gamma and pGA643-kappa These cDNAs are available from the Canadian Red Cross Society, Transfusion Dept., Sainte-Foy, Quebec.

Plant transformation, selection and intercrossing pGA643-gamma and pGA643-kappa were introduced into *A. tumefaciens* and the T-DNA was transferred into genotype 11.9 as described (Desgagnes et al 1995). Transgenic plants expressing the mRNAs for the kappa and gamma chains were intercrossed without emasculation. The progeny was screened by Northern hybridization and double-transgenics were tested for IgG content by Western blotting.

RNA isolation and Northern blot analyses

Total RNA was isolated from control and transgenic alfalfa leaves as described (de Vries et al 1988). Total RNA (15 $\mu$g/lane) was fractionated on 1% agarose-formaldehyde gels and transferred to Hybond-N nylon membranes. Hybridizations were performed using 32P-labelled probes consisting of a 0.6 kb EcoRI\Hinc II fragment from the kappa cDNA or the entire gamma chain cDNA.

Protein extraction and immunodetection

One gram of leaf tissue was homogenized in 5 mL of extraction buffer (50 mM Tris-HCl, pH 8.0, 1% SDS, 1%, $ mercaptoethanol) and sea sand. The homogenate was filtered through one layer of Miracloth and clarified by centrifugation (20,000 g, 20 min). For stability studies, homogenizations and S clarifications were carried out in distilled water and the extracts were brought to neutrality by adding 25 $\mu$g NaOH per g leaf fresh weight during homogenization. For studies in non-reducing conditions, extractions were carried out in 50 mM Tris-HCl, pH 7.5, 150 mM NaCl and 2 mM PMSF. Extracts were separated by SDS-polyacrylamide gel electrophoresis and electrotransferred onto a nitrocellulose membrane. Blocking of the membrane and detection of conjugated peroxidase activity was carried out with the BM chemiluminescence kit from Boehringer Manheim as described by the manufacturer. The first incubation was carried out with a rabbit anti-mouse antibody (Jackson ImmunoResearch Laboratories, West Grove, Pa.) at 4° C. Breakage of the disulfide bonds in the recombinant IgG was performed by bringing the sample to 0.4% $-mercaptoethanol with or without 10 mM sodium ascorbate and heating at 100° C. for 5 min.

Purification and characterization of plant mAb

Twenty g of leaf tissue were homogenized in 100 mL of extraction buffer A (50 mM Tris-base pH 7.4, 150 mM NaCl, 6 mM PMSF). The homogenate was filtered and clarified as described above. The supernatant was filtered on a Whatman paper and applied to an affinity column prepared by coupling human IgG to CNBr-Sepharose (Sigma). The column was washed with PBS and the antibody was eluted with a glycine buffer (100 mM, pH 2.3). The antibody-containing fractions were collected, neutralized with 0.1M Tris-HCl (pH 7.0) and dialysed against PBS. The amount of plant purified C5-1 and proteins present in extracts were measured as described (Bradford, 1976).

Hemagglutination assay

The reactivity of the plant C5-1 mAb against sensitized red blood cells was studied using the spin tube technique (Issit, 1985). Rh(o)-positive human red blood cells were sensitized by incubation with a human anti-Rh(D) reagent and washed with PBS. Forty μL of a 2% (v/v in PBS) suspension of sensitized red blood cells was added to 40 μL of C5-1 mAb at a known concentration in a glass test tube. The tubes were mixed and centrifuged for 20 sec at 500 g following a 5 min incubation at room temperature. The degree of agglutination was estimated visually. The titer is the reciprocal of the last dilution giving a positive agglutination reaction.

ELISA

The wells of microplates (Costar) were coated overnight with goat anti mouse or human IgG diluted at 5 μg/mL in a carbonate buffer (100 mM, pH 9.6). Blocking was done with PBS containing 0.25% casein (PBS-casein). Plant extracts were prepared as described previously for the affinity purification and applied directly to the wells following dilution in PBS-casein (1/10 and 1/100) to the coated plates. After incubation, the plates were washed and the binding of C5-1 was revealed using a goat anti-mouse IgG-peroxidase conjugate (Jackson Imm.Res.Lab). The enzyme conjugate was revealed with the orthophenylene diamine (Gibco BRL) substrate. Optical density at 490 nm was measured on a microplate reader (Dynatech MR 5000, Alexandria, Va., USA).

Example 1

In order to exemplify the usefulness of Alfalfa in the expression of proteins, including multimeric proteins such as mAbs, a high-affinity mAb was selected (C5-1) from a library of high-affinity murine anti-human IgG mAbs (St Laurent et al 1993). The C5-1 mAb gave a reactivity similar to commercial rabbit polyclonal reagents when tested with red blood cells weakly sensitized with blood group antibodies.

Integration and expression of transgenes in alfalfa.

Figure 1B:
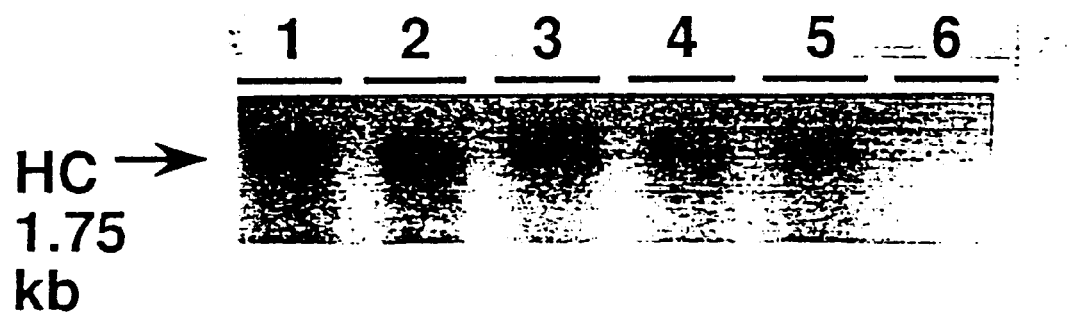
Figure 1C:
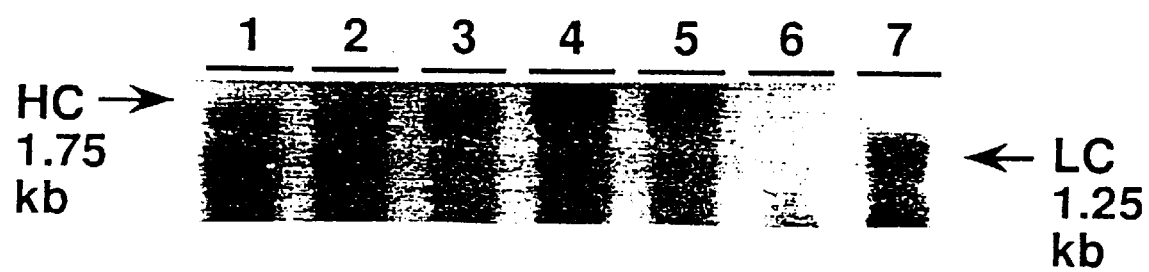

The cDNAs encoding the light and heavy chains of C5-1 were transferred into alfalfa plants following the protocol of Desgagnés et al (1995). Fifteen and 25 plants were obtained for the kappa and gamma chain respectively. The mRNA levels of the kappa and gamma chains were monitored by Northern hybridization. The probes hybridized specifically to mRNAs of approximately 1.25 kbp for the kappa chain (FIG. 1A) and 1.75 kbp for the gamma chain (FIG. 1B). Compared to murine cDNAs, the alfalfa derived mRNAs were approximately 250 bp longer, indicating that in both cases the polyadenylation signal of gene 7 was used. Seven out of 29 F1 plants analysed were found to express both H and L chain cDNAs simultaneously. FIG. 1C shows the variations obtained in the expression of kappa and gamma cDNAs in randomly chosen F1 progeny plants.

Expression and assembly of C5-1 mAb H and L chains in the F1 progeny.

Figure 2:
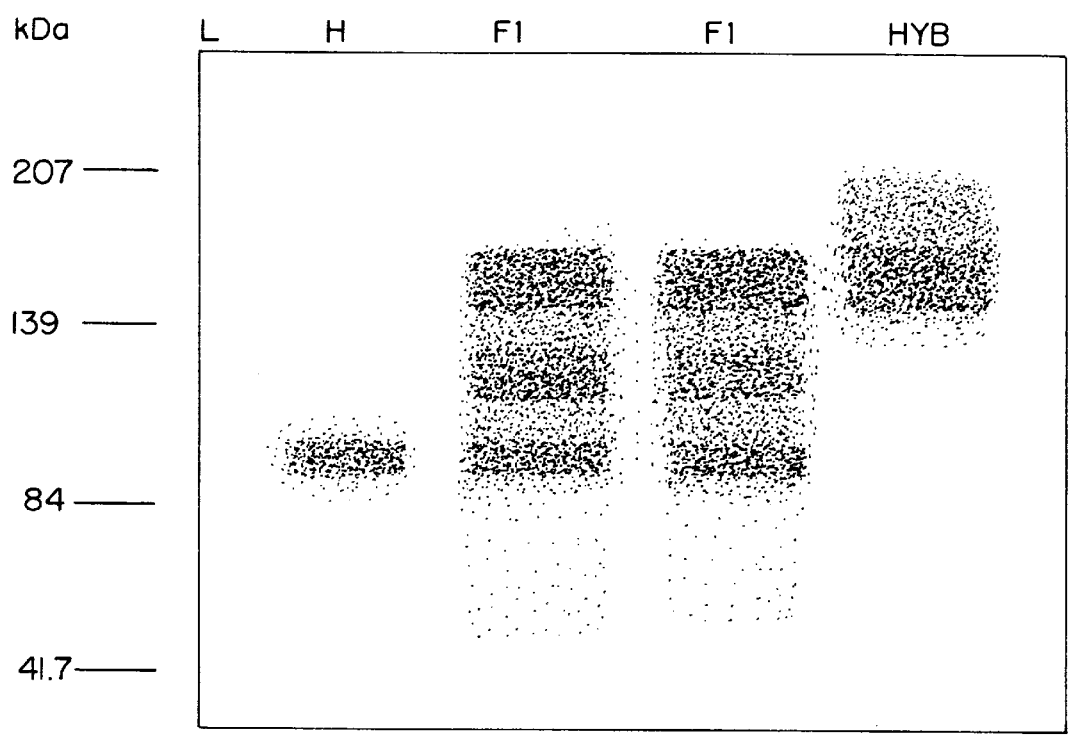
FIG. 2 shows the expression and assembly of C5-1 peptides in mono- and dual-transgenic alfalfa plants. Proteins were extracted without -mercaptoethanol in the presence of Tris-HCl (50 mM), PMSF (2 mM) and NaCl (150 mM). They were separated by SDS PAGE and electrotransfered onto a nitrocellulose membrane. C5-1 peptides were detected on the blots by using a rabbit anti-mouse IgG followed by an anti-rabbit IgG coupled to a peroxidase. Peroxidase activity was detected by chemiluminescence using the Boehringer Manheim BM chemiluminescence kit. Lane L: protein extract from a parental plant expressing the kappa cDNA. Lane H: protein extract from a parental plant expressing the gamma cDNA. Lanes F1: protein extracts from the F1 progeny expressing both the kappa and gamma cDNAs. Lane Hyb: C5-1 mAb isolated from hybridoma cells.

Randomly chosen F1 progeny plants exhibiting simultaneous expression of H and L chain cDNAs were analysed for the presence of the corresponding subunits by immunodetection. This initial screening demonstrated that all of them contained both mAb peptide chains (data not shown). Further analysis of one of these dual transgenics in comparison with corresponding parental plants showed that monotransgenics expressing the L chain cDNA did not accumulate significant amounts of the corresponding peptide, that monotransgenics expressing the H chain cDNA contained solely a dimer of H chains, and that dual-transgenics from the F1 progeny contained five assembly types, with molecular weights corresponding to the H2L2, H2L, H2, HL and H complexes (FIG. 2). The molecular weight of the fully assembled plant IgG (H2L2) was similar to that of hybridoma-derived C5-1 mAb. In order to break the disulfide bonds, samples were brought to 0.4% $-mercaptoethanol. In these conditions, all the immunoreactive material precipitated upon heating at 100° C. However, when ascorbate was added, the two constitutive subunits remained in solution and were separated on SDS-acrylamide gels. Separation in fully denaturing conditions showed that the constitutive subunits of plant-derived C5-1 are identical in size to these of hybridoma-derived C5-1 (data not presented).

Example 2

Affinity purification

Figure 3:
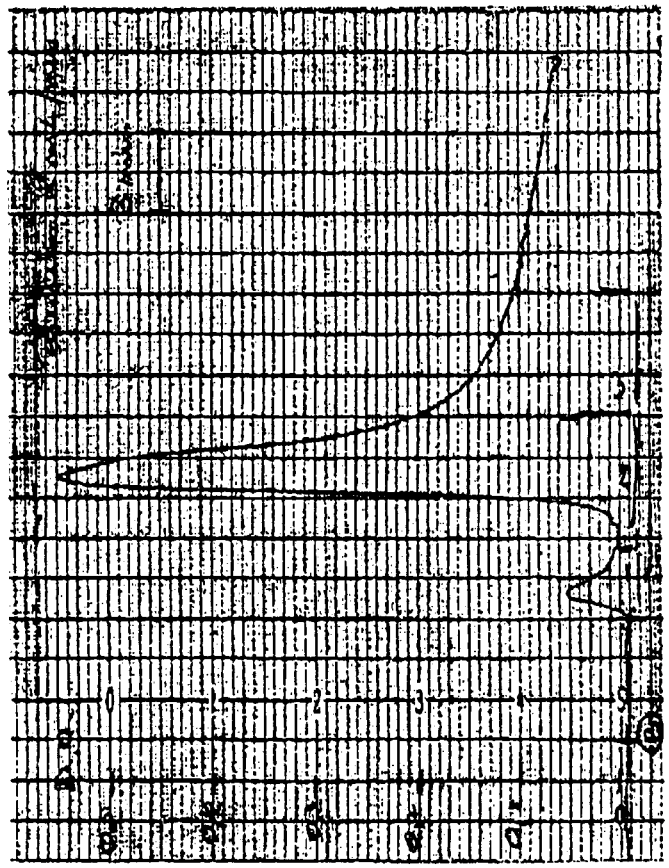
FIG. 3 shows the purification of plant C5-1. Elution profile, FIG. 3A, of purified C5-1 from expanded-bed affinity chromatography (STREAMLINE™-rProtein A matrix). Each fraction contained 1.5 mL of eluate from which 20 µL were loaded per lane, FIG. 3B and separated on SDS-PAGE in non-denaturing conditions and stained with Coomassie blue.
Figure 3:

Peptide content and stability of the alfalfa-derived C5-1 mAb. Affinity purification was used to recover the C5-1 mAb from leaf extracts of transgenic alfalfa plants (FIG. 3A). Quantitative measurements using leaf extracts from individual F1 dual-transgenic plants indicated that the level of C5-1 antibody ranged from 0.13 to 1.0% of total soluble protein. SDS-PAGE analysis of the purified protein under reducing conditions (FIG. 3B) showed that the two chains are detected by Coomassie Blue staining and that they have the same mobility as their counterparts from hybridoma cells. These results suggest that the plant-derived C5-1 was protected by glycosylation to the same extent as the C5-1 produced by the hybridoma cells.

Example 3

Stability of transgenic proteins produced in, and extracted from, alfalfa

Proteolysis of recombinant IgGs has been shown to occur in *Nicotiana tabacum* and *Arabidopsis thaliana* (Hiatt et al, 1989; Ma et al 1994). Although non-truncated IgGs are synthesized in plants with a signal peptide that promotes targeting to the inert extracellular matrix (De Wilde et al 1996), it has been observed that IgGs can be degraded by endogenous proteases upon extraction (Hiatt et al (1989), During et al (1990), Ma et al (1995), Ma and Hein (1995), Schouten (1996)). As this invention is directed to the preparation of single or multimeric proteins, such as the mAb C5-1, in alfalfa, the stability of such products was examined.

1) Stability of protein within alfalfa extracts, compared with tobacco extracts

Figure 4:
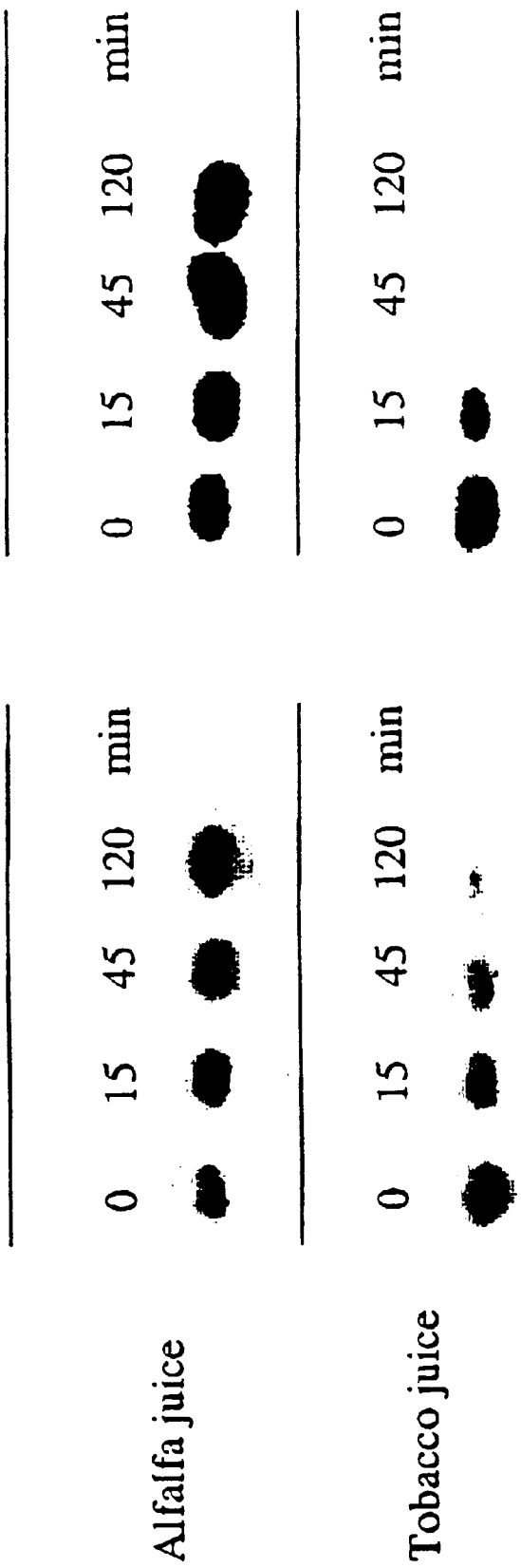
FIG. 4 shows a Western blot of C5-1 protein co-extracted in the presence of alfalfa or tobacco leaves. Two gms of alfalfa or tobacco leaf tissue were extracted in the presence of2 µg of transgenic or hybridoma culture produced C5-1. Extractions were performed at 0° C. with 10 mls of water, centrifuged at 20,000×g and incubated at 25° C. for up to 3 hours prior to Western analysis to determine the amount of C5-1 remaining within the extract solution.

In order to establish whether or not proteins are stable within crude extracts of alfalfa tissues, plant-derived, or hybridoma-derived, C5-1 was co-extracted in the presence of alfalfa (11.9 genotype) leaves in water, and left to incubate for up to 5 days at 25° C. During this incubation period aliquots were removed so that levels of C5-1 could be determined using Western analysis. The mAb, irrespective of the source was stable in alfalfa extracts prepared in water. Data for the first 3 hours of this example are presented in FIG. 4 however the same degree of stability was observed after a 5 day incubation period. Furthermore the mAb's were stable when prepared in a variety of buffers (data not shown). Also shown in FIG. 4 is the result of the same experiment, that of co-extracting C5-1 in the presence of tobacco tissues. It can be seen that levels of C5-1 incubated in the presence of tobacco extracts decrease over time and are not detectable after a three hour incubation period. Therefore, there is no need to add buffering salts, antioxidants, reducing agents, stabilizers, protease-inhibitors or the like as are typically added to the extraction medium in order to stabilize the transgenic protein of interest, such as the exemplary mAb, C5- for the extraction of transgenic proteins from alfalfa.

The stability of proteins in extracts of alfalfa was further investigated using monoclonal (25F5, human mAb), and polyclonal (hISG, human immunoglobulin) antibodies co-extracted with alfalfa in the absence of buffer as outlined above (see Table 1). The results indicate that there is a significant amount of immunologically detectable protein after 4 days incubation within alfalfa extracts stored at room temperature,

TABLE 1

Stability of proteins co-harvested with, and incubated within alfalfa extracts

| Time after extraction | C5-1 (μg/ml) | 2 5F5 (μg/ml) | hISG (μg/ml) |
| --- | --- | --- | --- |
| 0 | 5.2 ± 0.9 | 3.4 ± 0.2 | 7.7 ± 0.9 |
| 2 h | 4.9 ± 0.7 | 3.9 ± 0.5 | 7.1 ± 0.8 |
| 6 h | 4.1 ± 0.2 | 4.0 ± 0.5 | 6.0 ± 0.6 |
| 1 d | 4.6 ± 0.5 | 0.8 | 5.6 ± 0.3 |
| 4 d | 4.3 ± 0.1 | 0.75 ± 0.03 | 3.4 ± 0.1 |
| 12 d | 0.58 ± 0.07 | 0.18 ± 0.02 | 1.8 ± 0.1 |

2) Stability of recombinant protein during extraction from transgenic alfalfa plants Stability of transgenic C5-1 in crude extracts was also demonstrated by homogenization of the leaves of dual-transgenics in pure water. Such leaf extracts had a small but significant buffering capacity which was established at ca 0.4 pH unit (between pH 6.5 and pH 8.5) per mole NaOH in extracts containing 100 g of fresh leaves. Results show that these extracts can be kept at room temperature without significant changes in pH for at least two hours. Water alone was as good an extractant for transgenic C5-1 as buffers containing protease inhibitors (buffer A), and C5-1 remained 100% stable at room temperature for at least two hours within this minimal extraction system (Table 2).

TABLE 2

Stability of plant C5-1 in crude protein extracts

| Time after extraction | Total proteins (mg/g) | C5-1* (μg/mL) |
| --- | --- | --- |
| Control | 2.21 | 2.40 |
| 0 hour | 2.47 | 2.45 |
| 1 hour | 2.32 | 2.45 |
| 2 hours | 2.24 | 2.62 |

*Determined by murine IgG-specific ELISA

3) Stability of protein within harvested plant tissues

Figure 5:
FIG. 5 shows PAGE and Western blot analysis of proteins obtained from aerial portions of a dual transgenic alfalfa plant expressing C5-1 that were cut and allowed to dry at room temperature for up to five days. Equal amount of harvested tissues were maintained at a relative humidity of 20% for 0 h, 7 h, 1 day, 2 days, and 5 days before extracting and determining protein profiles (FIG. 5A), and assaying for levels of C5-1 using Western analysis (FIG. 5B).
Figure 5:
Figure 6:
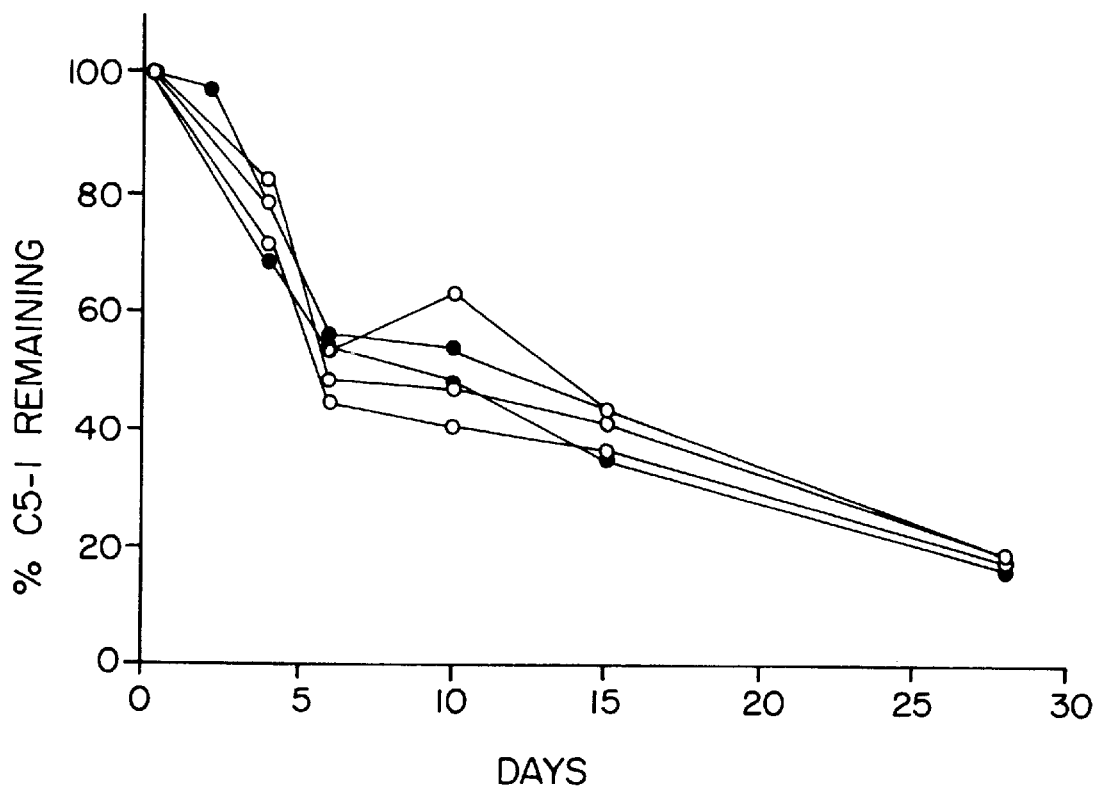
FIG. 6 shows the stability of plant-derived (●) and hybridoma-derived (○) C5-1 within mice over a one month period, following intravenous injection. Detection was performed with an ELISA against immobilized human IgG.

To determine whether drying of aerial portion of alfalfa had any effect on the levels of C5-1 and/or the ability to extract C5-1 from transgenic aerial tissues, a dual transgenic was harvested and left to dry at 25° C., relative humidity of 20% for up to 30 days. At the end of this drying period, the water content of the leaf material was below 20%, which would be the level observed under field conditions. Equal amounts of leaf material were harvested during this drying period, extracted and levels of C5-1 assayed using Western analysis. As can be seen in FIG. 5, which shows the data over the first 5 days, there was no decrease observed in the amount of extractable transgenic protein from drying, or dried alfalfa leaves. The same result is observed after drying for 30 days when plants were harvested and maintained under field conditions.

4) Stability of C5-1 after administration to mice

Equal amounts of alfalfa-, or hybridoma-derived C5-1 were intravenously administered to mice and the occurrence of the protein was determined within samples of plasma obtained over a 28 day period. The results of this experiment are displayed in FIG. 6. The half-life of the administered C5-1 protein within mice was the same for either the hybridoma or plant derived protein. This suggests that plant-derived C5-1 is protected by glycosylation to a similar extent as that of the hybridoma-derived protein. Following a 50% loss of injected protein over a 5 day period, the remaining protein decreased a further 25% over the next 20 day period. At the end of the assessment period, 25% of the initially supplied protein was detectable within mice.

5) Stability of protein within propagules of alfalfa

In order to establish the stability of the expression of transgenic proteins within propagules of transgenic alfalfa, 15 plants of two genotypes derived from the F1 progeny were examined for concentration of C5-1 within leaf tissues. Propagules were prepared by inducing root formation on internodal stem sections. Fifteen of the regenerated plants from the two genotypes were analysed for their C5-1 content and compared to the levels of C5-1 within the parent material. The data presented in Table 3 shows the results of such an experiment and indicates that the levels of C5-1 remain constant between that observed within the parent and propagated materials.

TABLE 3

Stability of extractable C5-1 between Generations

| Genotype 2 Starting material* 14.4 μg/g leaf | Genotype 3 Starting material 14.4 μg/g leaf |
| --- | --- |
| 1: 21.2 μg/g | 16 : 13.4 μg/g |
| 2: 17.9 μg/g | 17 : 18.2 μg/g |
| 3: 16.9 μg/g | 18 : 19.7 μg/g |
| 4: 18.5 μg/g | 19 : 15.1 μg/g |

TABLE 3-continued

Stability of extractable C5-1 between Generations

| Genotype 2<br>Starting material*<br>14.4 μg/g leaf | Genotype 3<br>Starting material<br>14.4 μg/g leaf |
|---|---|
| 5: 17.8 μg/g | 20 : 14.5 μg/g |
| 6: 15.0 μg/g | 21 : 15.6 μg/g |
| 7: 16.1 μg/g | 22 : 14.6 μg/g |
| 8: 14.4 μg/g | 23 : 12.4 μg/g |
| 9: 21.8 μg/g | 24 : 15.6 μg/g |
| 10: 14.2 μg/g | 25 : 17.5 μg/g |
| 11: 18.4 μg/g | 26 : 17.4 μg/g |
| 12: 18.2 μg/g | 27 : 18.0 μg/g |
| 13: 17.3 μg/g | 28 : 16.8 μg/g |
| 14: 15.1 μg/g | 29 : 17.2 μg/g |
| 15: 12.7 μg/g | 30 : 14.6 μg/g |
| 17.0 ± 2.53 μg/g | 16.0 ± 1.99 μg/g |

*The initial value of 14.4 had been determined in a previous experiment

Example 4
Antigen-binding and hemagglutinating activities

The plant-derived C5-1 mAb was further tested for its antigen binding capacity using an ELISA test. Serial dilutions of leaf extract from plants producing C5-1 were used for this test. Table 4A presents values of optical densities obtained with the 1/10 dilution samples. The results showed that the plant C5-1 mAb is recognized by the anti-mouse IgG antibodies suggesting that the overall conformation of the plant produced antibody is that of an IgG. Furthermore the plant C5-1 specifically recognized human IgG indicating the proper folding of the H and L chains to form the antigen-binding site. Preliminary testing indicated that the C5-1 plant extract could specifically agglutinate red blood cells sensitized with human IgG. A more complete characterization was carried out on the affinity-purified material in parallel with the hybridoma-derived C5-1 mAb. Results (Table 4B) showed that the plant-derived C5-1 mAb specifically agglutinated anti-D-sensitized human RBC giving a complete (4+) reaction at 6 μg/mL, which is similar to that observed with hybridoma-derived C5-1 mAb.

The ELISA assay with anti-murine IgG as coating antibody was also used to determine reactivity of parental transgenics. Table 5A shows that no signal was detected in L-monotransgenics, and that a signal was detected in plants containing the H chains. These results were used to determine the amount of immunoreactive material in crude extracts. Known quantities of crude reactive material were then tested for specific activities in wells coated with human IgGs (Table 5B). This second experiment showed that the heavy chains alone cannot react with human IgGs. It also shows that the plant H2L2 has a specific activity similar to that of C5-1 from hybridoma cells. True affinity of the plant-derived antibody for its antigen was compared to that of hybridoma-derived antibody by measuring dissociation constants at equilibrium. $K_D$s were $4.7 \times 10^{-10}$ and $4.6 \times 10^{-10}$M for plant- and hybridoma-derived C5-1 respectively.

TABLE 4

Reactivity of the plant-derived C5-1 mAb
(A) ELISA assay; (B) Hemagglutination

| A)<br>Material tested | Optical density at 490 nm<br>Immobilized antibodies | |
|---|---|---|
| | Goat antimouse | Human IgG |
| Control plant | 0.000 ± 0.000 | 0.000 ± 0.000 |
| extract (1/10) | | |
| Transgenic plant extract (1/10) | 0.243 ± 0.007 | 0.531 ± 0.014 |
| C5-1 hybridoma supernatant (1/10) | 0.414 ± 0.034 | 0.643 ± 0.035 |

| B)<br>Sample | Hemagglutination strength | |
|---|---|---|
| | Uncoated RBC | Anti-D-coated RBC |
| None | – | – |
| Control anti-human IgG reagent | – | ++++ |
| Hybridoma C5-1 (6 Fg/mL) | – | ++++ |
| Plant C5-1 (6 Fg/mL) | – | ++++ |

TABLE 5

Immunoreactivity
(A) and specific activity (OD per 100 ng)
(B) of parental and F1 transgenic plants

| A)<br>Extract | Optical density | Fg/mL |
|---|---|---|
| IgG from hybridoma cells | 0.376 ± 0.008 | 0.28* |
| L (1/1) | 0.000 | — |
| H (1/4) | 0.560 ± 0.049 | 0.10 ± 0.01** |
| HL (F1, 1/6) | 0.328 ± 0.027 | 0.25 ± 0.02 |

| B)<br>Extract | Optical density | Specific activity |
|---|---|---|
| IgG from hybridoma cells | 0.332 ± 0.032 | 0.235 ± 0.020 |
| L (1/1) | 0.000 | — |
| H (1/1) | 0.000 | — |
| HL (F1, 1/32) | 0.334 ± 0.011 | 0.267 ± 0.080 |

*From a purified fraction at 0.28 μg/mL
**Calculated on the basis of $H_2L_2$ structure Example 5
Large-scale purification of plant C5-1

Three hundred g of plant material was homogenized in 1.2 L of an extraction buffer containing 50 mM borate and 4M NaCl at pH 9.0. The homogenate was clarified through filtration on a cheese cloth. This homogenate was then loaded directly by upward flow on an expanded bed of Streamline rProtein A matrix (Pharmacia). Loading was performed at 4° C. at a rate of 7 mL/min. The column was washed with 250 mL of the extraction buffer and eluted with 50 mM sodium citrate, 50 mM sodium phosphate and 300 mM NaCl at pH 3.0. Fractions (1.5 mL) were recovered and immediately neutralized with 100 μL of 1.5M Tris at pH 8.8.

Expanded bed adsorption (STREAMLINE™ r Protein A) was chosen to allow loading of partially clarified plant extracts containing colloidal material at a high-flow rate. Using this technology, plant C5-1 was purified from non clarified crude plant extract as a single peptide as shown by Coomassie staining on SDS-PAGE gels (FIG. 3B).

All Scientific publications and patent documents are incorporated herein by reference.

The present invention has been described with regard to preferred embodiments. However, it will be obvious to persons skilled in the art that a number of variations and modifications can be made without departing form the scope of the invention as described in the following claims.

References

An, G., Ebert, P. R., and Ha, S. B. 1988. A3 pp. 1—in *Plant Mol. Biol. Manual,* Gevin, S. B., and Shilperoot, R. A. (eds) Kluwer Academic Publisher, Dordrecht.

Austin S., Bingham E. T. 1997 The Potential Use of Transgenic Alfalfa as a Bioreator for the Production of Enzymes. in *Biotechnology and the Improvement of Forage Legumes.* McKersie B. D. and Brown D. C. W. (eds) CAB International Bradford, M. M. 1976. A rapid and sensitive method for the quantitation of microgram quantities of protein utilizing the principle of protein dye binding. Anal Biochem 72: 248–254.

De Wilde, C., De Neve, M., De Rycke, R., Bruyns, A.-M., De Jaeger, G., Montagu, M. V., Depicker, A., and Engler, G. 1996. Intact antigen-binding MAK33 antibody and Fab fragment accumulate in intracellular spaces of *Arabidopsis thaliana.* Plant Science. 114:233–241.

de Vries, S., Hoge, H., and Bisseling, T. 1988. B6 pp 1—in Plant Mol. Biol. Manual, Gevin, S. B., and Shilperoot, R. A. (eds) Kluwer Academic Publisher, Dordrecht.

Desgagnés, R., Laberge, S., Allard, G., Khoudi, H., Castonguay, Y., Lapointe, J., Michaud, R., and Vézina, L.-P. 1995. Genetic transformation of commercial breeding lines of alfalfa (*Medicago sativa*). Plant Cell Tissue Organ Culture. 42:129–140.

During, K., Hippe, S., Kreuzaler, F., and Schell, J. 1990. Synthesis and self-assembly of a functional monoclonal antibody in transgenic *Nicotiana tabacum.* Plant Mol. Biol. 15:281–293.

Geierson and Corey (1988), Plant Molecular Biology, 2d Ed.

Hiatt, A., Caferky, R., and Bowdish, K. 1989. Production of antibodies in transgenic plants. Nature 342:76–78.

Hiatt, A. 1990. Antibodies produced in plants. Nature 344:469–470

Hiatt, A., and Pinney, R. 1992. pp. 159–176 in Antibody expression and engineering A practical guide Borrebaeck, C. A. K. (ed) Freeman W. H. and company., New York.

Issit, P. D. 1985. Applied blood group serology. Montgomery Scientific Publications, Miami.

Jones , B. A. et al 1995 Characterization of proteolysis in alfalfa and red clover. Crop Sc. 35:537–541.

Ma, J. K.-C., Leehner, T., Sabtila, P., Fux, C. I., and Hiatt, A. 1994. Assembly of monoclonal antibodies with IgG1 and IgA heavy chain domains in transgenic tobacco plants. Eur. J. Immunol. 24:131–138.

McKersie, B. D., and Bowley, S. R. 1993. pp 231–255 in Synseed. Redenbaugh (ed) CRC Press.

Miele, L. 1997 Plants as bioreactors for biopharmaceuticals: regulatory considerations. TIBTECH 15:45–50.

Morris P., and Robbins M. P. 1997 Manipulating Condensed Tannins in Forage Legumes. in *Biotechnology and the Improvement of Forage Legumes.* McKersie B. D. and Brown D. C. W. (eds) CAB International.

Papadopoulos, Y. A., McKersie, B. D. 1983 A comparison of protein degradation during wilting and ensiling of 6 forage species. Can. J. Plt. Sc. 63:903–912.

St Laurent, M., Marcil, A., Verrette, S., and Lemieux, R. 1993. Functional cooperation among human IgG-specific murine monoclonal antibodies for the detection of weak blood group antibodies in routine agglutination tests. Vox Sang. 64:99–105.

Wang, H. Y., and Imanaka, T. 1995. Antibody expression and engineering. American chemical society, Washington, D.C.

Weissbach and Weissbach, (1988) Methods for Plant Molecular Biology, Academy Press, New York VIII, pp. 421–463.

Whitelam, G. C., and Cockburn, W. 1996. Antibody expression in transgenic plants. Trends in Plant Science 8: 268–272.

Wongsamuth and Doran, 1997. Production of monoclonal antibodies by tobacco hairy roots. Biotechnology and Bioengineering. 54, 401–415.

Wright, A., Shin, S-U and Morrison, S. L. 1992. Genetically engineered antibodies: progress and prospects. Crit. Rev. Immunol. 12, 125–168.

The embodiments of the invention in which an exclusive property of privilege is claimed are defined as follows:

1. A method for the stable production of an extractable protein comprising:
   a) selecting an alfalfa genotype wherein said genotype:
      i) is perennial;
      ii) exhibits embryogenic potential;
      iii) is transformable; and
      iv) exhibits negligible proteolytic activity in extracts over at least a three hour period;
   b) transforming at least one alfalfa plant of the genotype selected in step a) with a vector comprising a gene encoding said protein to produce at least one transformed alfalfa plant;
   c) confirming the presence of said gene in said at least one transformed alfalfa plant;
   d) growing said at least one transformed alfalfa plant, so as to produce said protein;
   e) harvesting aerial portions from said at least one transformed alfalfa plant or from at least one transformed progeny alfalfa plant produced from a propagule of said at least one transformed alfalfa plant;
   f) extracting said protein from tissues of said aerial portions that were harvested in step e);
   g) allowing said at least one transformed alfalfa plant or said at least one transformed progeny alfalfa plant to re-grow said aerial portions; and
   h) repeating steps e) to g) to produce a continuous, stable supply of said protein.

2. The method of claim 1, wherein the extracting is conducted in the absence of protease inhibitors, antioxidants, reducing agents or stabilizers.

3. The method of claim 2, wherein the extracting is conducted in water.

4. The method of claim 1, further comprising drying said harvested aerial portions after said harvesting of step e) and prior to said extracting of step f).

5. The method of claim 1, wherein the propagule is a stem-derived propagule.

6. The method of claim 1, wherein the propagule is an embryo-derived propagule.

7. The method of claim 1, wherein said protein is a monoclonal antibody, and wherein step b) comprises transforming a first alfalfa plant with a vector comprising a gene encoding the heavy chain of said monoclonal antibody to produce a first transformed alfalfa plant and transforming a second alfalfa plant with a vector comprising a gene encoding the light chain of said monoclonal antibody to produce a second transformed alfalfa plant, and then crossing said first transformed alfalfa plant and said second transformed alfalfa plant to produce said at least one transformed alfalfa plant, wherein said at least one transformed alfalfa plant expresses both the heavy chain and the light chain of said monoclonal antibody.

8. The method of claim 1, further comprising purifying said protein after said extracting of step f) and prior to said allowing of step g).

9. The method of claim 8, wherein the step of purifying the protein is performed by using affinity chromatography.

10. The method of claim 1 wherein said alfalfa genotype is 11.9.

\* \* \* \* \*